US00PP23511P3

(12) United States Plant Patent
Nielsen

(10) Patent No.: US PP23,511 P3
(45) Date of Patent: Apr. 2, 2013

(54) ***OSTEOSPERMUM* PLANT NAMED 'DAOSFEMTEN'**

(50) Latin Name: *Osteospermum ecklonis*
Varietal Denomination: DAOSFEMTEN

(75) Inventor: Rune Harboe Nielsen, Odense N (DK)

(73) Assignee: Dalina APS, Odense N (DK)

( * ) Notice: Subject to any disclaimer, the term of this patent is extended or adjusted under 35 U.S.C. 154(b) by 42 days.

(21) Appl. No.: 13/064,615

(22) Filed: Apr. 4, 2011

(65) Prior Publication Data

US 2012/0255083 P1 Oct. 4, 2012

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

Printout of application information from Community Plant Variety Office (CPVO) website for corresponding CPVO application No. 2010/0797 filed Apr. 6, 2010 (1 page) (http://www.cpvoextranet.cpvo.europa.eu).

Printout of application information from Canadian Food Inspection Agency—Plant Varieties Journal No. (date) for corresponding Canadian Plant Breeders' Rights application No. 10-6963 filed May 3, 2010 (1 page) (http://www.inspection.gc.ca/english/plaveg/pbrpov/joubule.shtml).

*Primary Examiner* — Susan McCormick Ewoldt
(74) *Attorney, Agent, or Firm* — Foley & Lardner LLP

(57) ABSTRACT

A new distinct cultivar of *Osteospermum* plant named 'DAOSFEMTEN', characterized by its vigorous growth, with globular, upright to spreading shape; very well branching habit (10-15 per plant), with medium strong lateral stems and thick leaves; color of leaves RHS 139A (upper side) and RHS 137B (Underside); ray florets with a unique color combination, pure white (as the white space between the color samples on the RHS colour chart), and violet-blue (RHS 97C) with darker violet-blue stripes (RHS 97A) and stains of yellow (RHS 162C) at the tip, on the underside; and disc florets that appear Violet-Blue (RHS 96A).

5 Drawing Sheets

Latin name of the genus and species of the claimed plant: *Osteospermum ecklonis*.

Variety denomination: 'DAOSFEMTEN'.

BACKGROUND OF THE INVENTION

The present invention relates to a new and distinct cultivar of *Osteospermum* plant, botanically known as *Osteospermum ecklonis* (DC) T. Norl., commonly known as Cape Daisy and and hereinafter referred to by the cultivar name 'DAOSFEMTEN'.

The new *Osteospermum* cultivar is a product of a planned breeding program conducted by the inventor, Rune Nielsen, in Stige, Denmark. The objective of the breeding program is to develop a new *Osteospermum* cultivar with good garden performance, well branching growth, continuous flowering and an attractive inflorescence color.

The new *Osteospermum* cultivar originated from a cross made in a controlled breeding program by the inventor in 2006, in Stige, Denmark. The female or seed parent is *Osteospermum* cultivar designated 'Cape Daisy® Zanzibar White'. The male or pollen parent is a creme coloured *Osteospermum* variety designated 5300A (not patented).

Asexual reproduction of the new *Osteospermum* cultivar by terminal cuttings was first performed in November, 2007 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAOSFEMTEN', which in combination distinguish this *Osteospermum* as a new and distinct cultivar:

1. Vigorous cultivar, with globular upright to spreading shape;
2. Well branching (10-15 per plant) with medium strong lateral stems and thick leaves. Color of leaves RHS 139A (upper side) RHS 137B (Underside);
3. Ray florets with a unique color combination, pure white (as the white space between the colour samples on The RHS colour chart), and violet-blue (RHS 97C) with darker violet-blue stripes (RHS 97A) and stains of yellow (RHS 162C) at the tip, on the underside; and
4. Disc florets that appear Violet-Blue (RHS 96A).

Plants of the new *Osteospermum* 'DAOSFEMTEN' differ from plants of the parents, 'Cape Daisy® Zanzibar® White' and 5300A (unpatented) in the traits described in Table 1.

TABLE 1

Comparison with Parental Cultivars

| Trait | New Cultivar 'DAOSFEMTEN' | Female Parent 'Cape Daisy ® Zanzibar ® White' | Male Parent 5300A (unpatented) |
|---|---|---|---|
| Plant Size | | | |
| Height: | About 14 cm. | About 13 cm. | About 15 cm. |
| Diameter: | About 20 cm. | About 18 cm. | About 20 cm. |

TABLE 1-continued

| Comparison with Parental Cultivars | | | |
|---|---|---|---|
| Trait | New Cultivar 'DAOSFEMTEN' | Female Parent 'Cape Daisy ® Zanzibar ® White' | Male Parent 5300A (unpatented) |
| Overall Plant Shape | globular upright to spreading shape. | globular upright to spreading shape. | globular upright to spreading shape. |
| Stem | | | |
| Length: | About 2-5 cm. | About 2-5 cm. | About 4-6 cm. |
| Diameter: | About 4 mm. | About 4 mm. | About 5 mm. |
| Strength: | Medum strong. | Medum strong. | Very strong. |
| Color: | RHS 145B (yellow-green). | RHS 146D (yellow-green). | RHS 144A (yellow-green). |
| Number of Flowers per Plant: | About 40. | About 20. | About 20. |
| Flower Size | | | |
| Depth: | About 10 mm. | About 10 mm. | About 12 mm. |
| Diameter: | About 7 cm. | About 6 cm. | About 8 cm. |
| Mature Petal Color (upper side): | Pure white (as white as the space between the colour samples on the RHS colour chart). | Pure white, with a 2 mm Purple N79B and N78C ring around the base. | RHS 155C (white). |
| Mature Petal Color (underside): | RHS 97C (violet-blue) with darker stripes RHS 97A (violet-blue) and stains of RHS 162C (greyed-yellow) at the tip. | RHS 97C (violet-blue) with darker stripes RHS N92D (violet-blue). | RHS 162A (greyed-yellow) |

Of the many commercial cultivars known to the present inventor, the most similar in comparison to the new *Osteospermum* 'DAOSFEMTEN' is the *Osteospermum* ('Cape Daisy® Zanzibar® White', in the characteristics described in Table 2.

TABLE 2

| Comparison with Comparison Cultivars | | |
|---|---|---|
| Trait | New Cultivar 'DAOSFEMTEN' | 'Cape Daisy ® Zanzibar ® White' |
| Plant Size | | |
| Height: | About 14 cm. | About 13 cm. |
| Diameter: | About 20 cm. | About 18 cm. |
| Overall Plant Shape | globular upright to spreading shape. | globular upright to spreading shape. |
| Stem | | |
| Length: | About 2-5 cm. | About 2-5 cm. |
| Diameter: | About 4 mm. | About 4 mm. |
| Strength: | Medum strong. | Medum strong. |
| Color: | RHS 145B (yellow-green). | RHS 146D (yellow-green). |
| Number of Flowers per Plant: | About 40. | About 20. |
| Flower Size | | |
| Depth: | About 10 mm. | About 10 mm. |
| Diameter: | About 7 cm. | About 6 cm. |
| Mature Petal Color (upper side): | Pure white. (As white as the space between the colour samples on the RHS colour chart). | Pure white, with a 2 mm Purple N79B and N78C ring around the base. |
| Mature Petal Color (underside): | RHS 97C (violet-blue) with darker stripes RHS 97A (violet-blue) and stains of RHS 162C (greyed-yellow) at the tip. | RHS 97C (violet-blue) with darker stripes RHS N92D (violet-blue). |

BRIEF DESCRIPTION OF THE PHOTOGRAPHS

The accompanying photographs illustrate the overall appearance of the new *Osteospermum* 'DAOSFEMTEN' showing the colors as true as is reasonably possible with colored reproductions of this type. Colors in the photographs may differ slightly from the color value cited in the detailed botanical description which accurately describe the color of 'DAOSFEMTEN'.

DETAILED BOTANICAL DESCRIPTION

Figure 1:
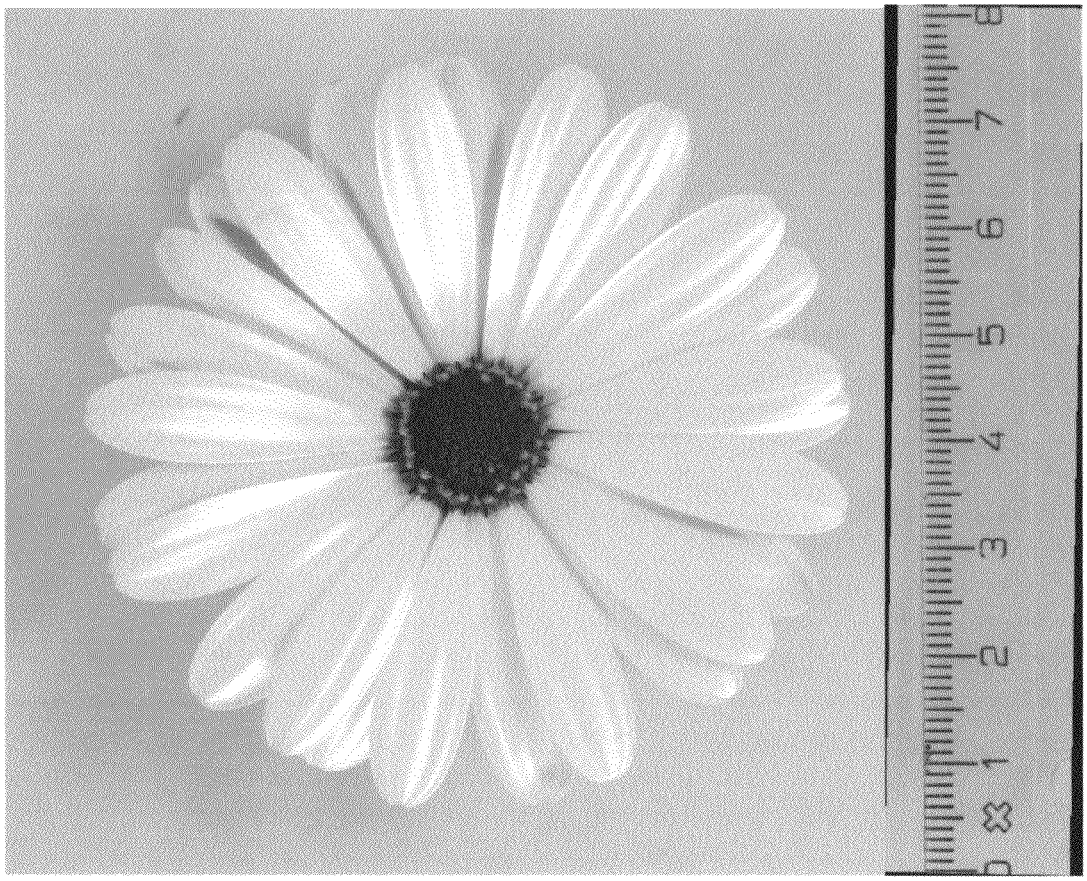
FIG. 1 shows a close-up view of the composite flower head from 'DAOSFEMTEN'.
Figure 2:
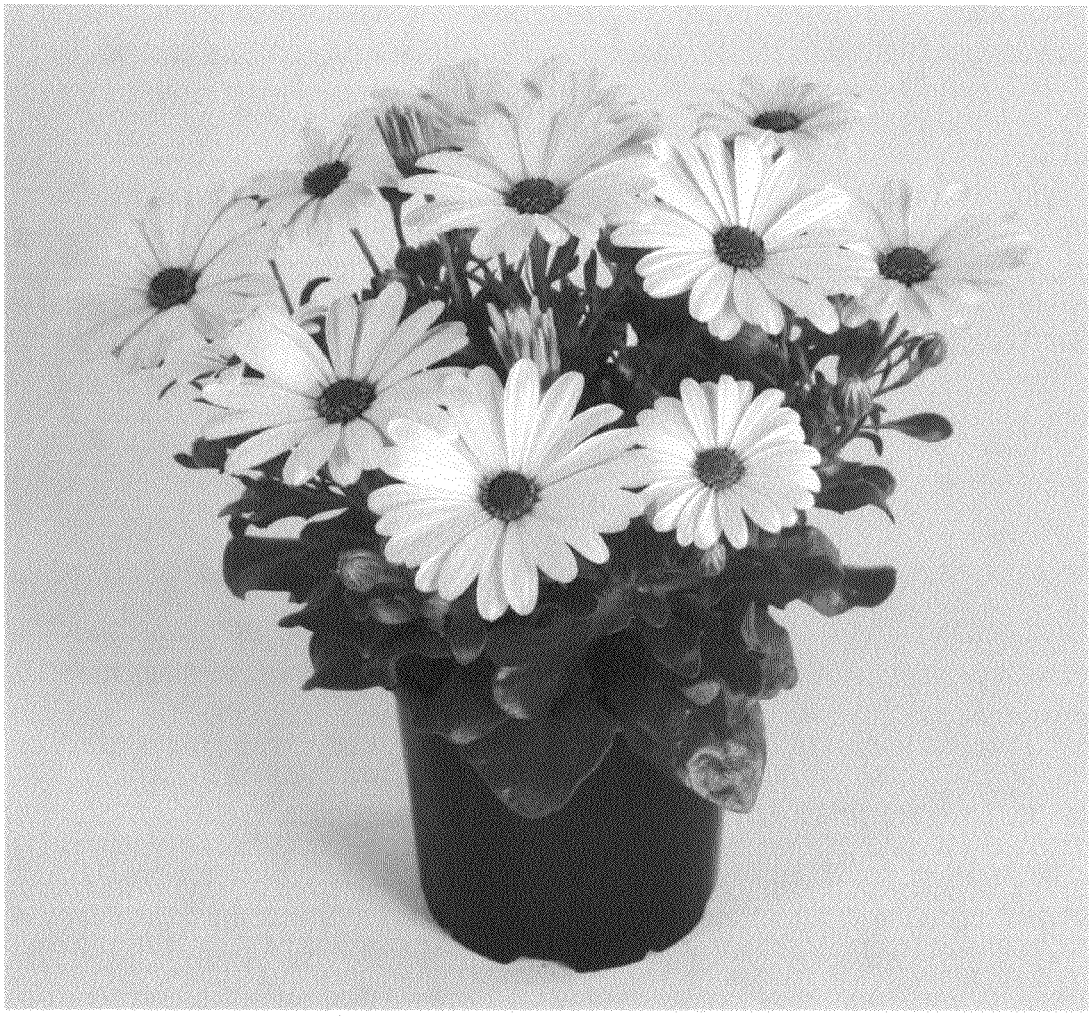
FIG. 2 shows a side view perspective of a typical flowering plant of 'DAOSFEMTEN' in a 11 cm pot, at 12 weeks of age after planting.
Figure 3:
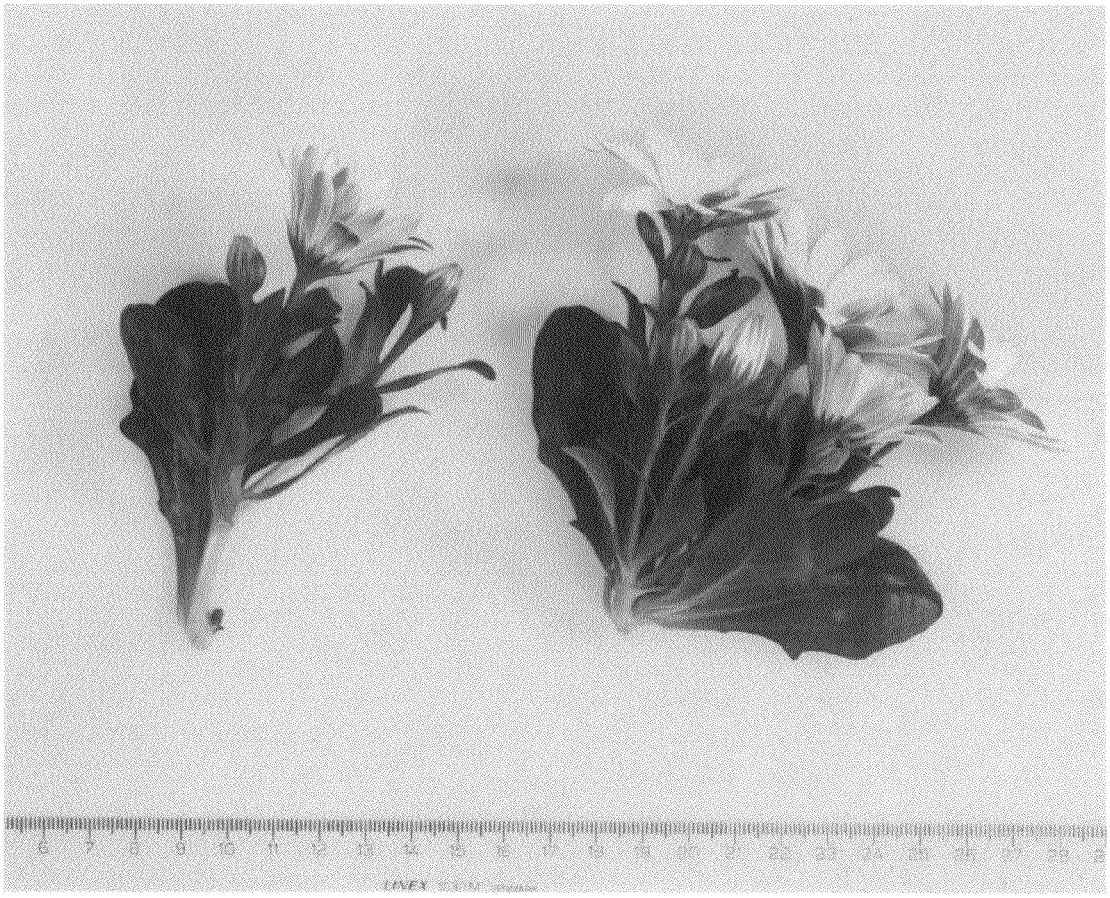
FIG. 3 shows a close-up view of the typical lateral stems with leaves and buds of 'DAOSFEMTEN'.
Figure 4:
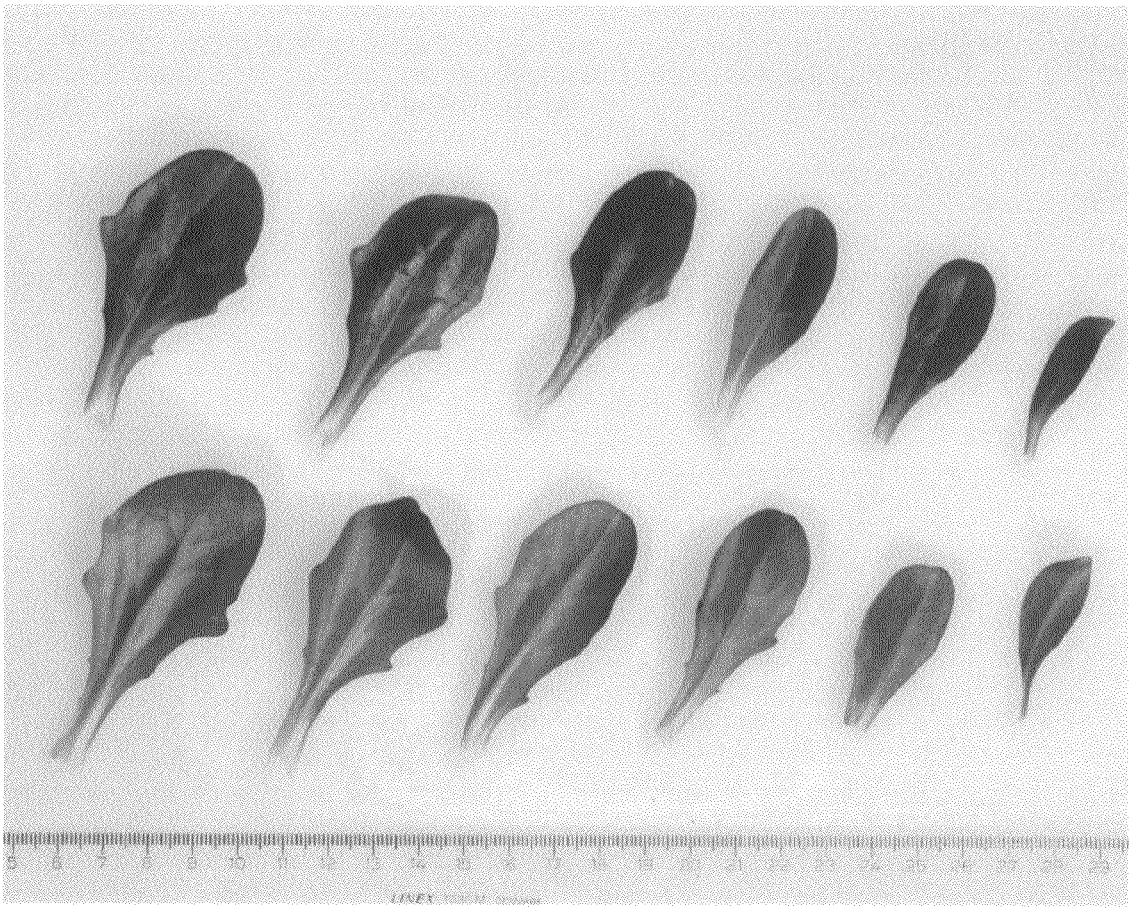
FIG. 4 shows a close-up view of the different leaf sizes of 'DAOSFEMTEN'.
Figure 5:
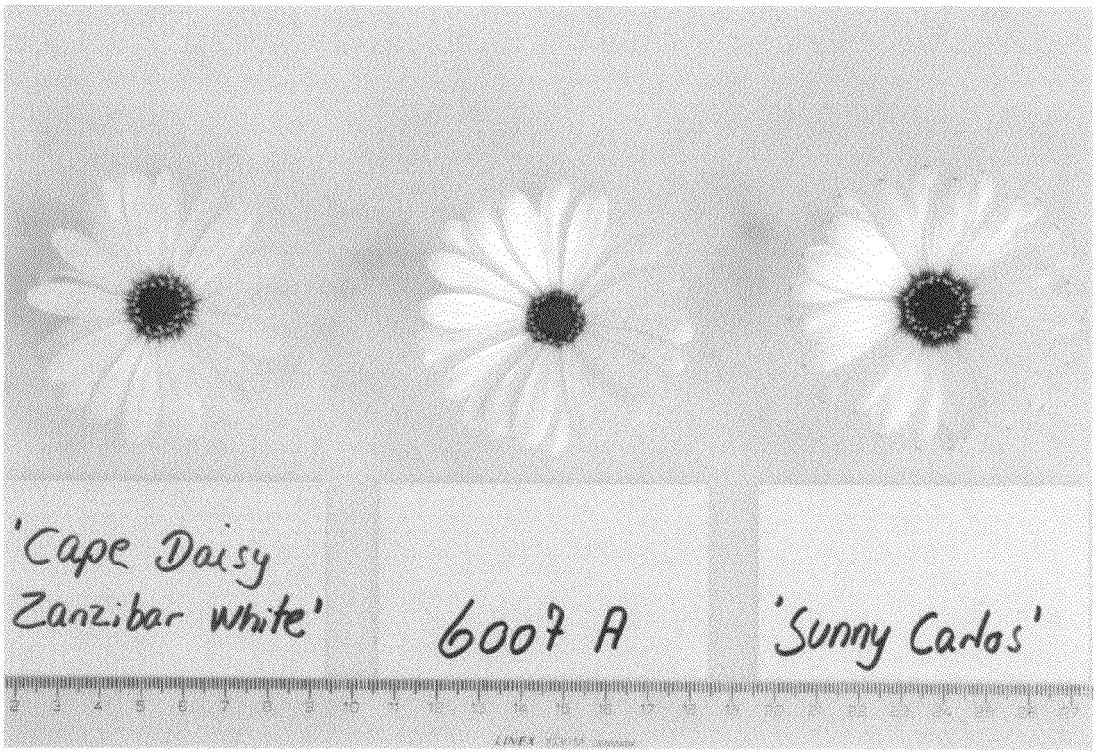
FIG. 5 shows a comparison between 'Cape Daisy® Zanzibar White' (female parent)', 'Sunny® Carlos' and 'DAOSFEMTEN' (Breeders reference: 6007A).

The new *Osteospermum* 'DAOSFEMTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Osteospermum* 'DAOSFEMTEN' as grown in a glasshouse, equipped with heat, assimilation light and ebb/flood watering system in Odense, Denmark, under conditions which closely approximate those generally used in commercial practice. The plants was grown in 14° C., with a venting temperature on 16° C. Assimilation light was given when natural daylight was below 3000 lux and the day length was extended to 16 hours. The EC levels in the soil was kept at about 2.5-3.5 and pH around 6.0 during the production. Plant growth was regulated 3 times during the production period, using 3‰ Cycocel (chlormequat-chloride) as a drench (80-100 ml/pot).

Color references are made to The Royal Horticultural Society Colour Chart (R.H.S.), Colour Chart 2001 edition, Color values were taken under March daylight conditions at approximately 10:00-14:00 in Stige, Denmark. The age of the 'DAOSFEMTEN' plants described is 12 weeks from potting.

Classification:

*Botanical.—Osteospermum ecklonis* (DC) Norl.

Parentage:

*Female or seed parent.—Osteospermum* cultivar designated 'Cape Daisy® Zanzibar® White'.

*Male or pollen parent.*—*Osteospermum* variety designated 5300A (Unpatented).

Propagation:

*Type.*—Vegetative terminal cuttings.

*Time and temperature to initiate roots.*—About 9 to 13 days at 19 to 21° C. in tunnels in a greenhouse.

*Time and temperature to produce a rooted young plant.*—About 4 to 5 weeks at 18° (initiation period benefits from 19-21° C.).

*Rooting habit.*—Vigorous, white and well branched.

Plant description:

*General appearance and form.*—Globular, upright, with basal branching. Inflorescences in composite heads. Freely branching with lateral flowering branches forming at every node.

*Growth rate.*—Growing about 1 cm per week during production period.

*Plant height.*—About 13 cm to 16 cm.

*Plant width* (*spread*).—About 18 cm to 21 cm.

*Crop time to produce a mature flowering plant.*—It requires 4-5 weeks to produce a young plant in a 35 mm propagation plug. After potting 12-14 weeks are required to produce finished flowering plants in 11 cm pots.

Stem:

*Shape.*—Round.

*Length.*—About 2 cm to 5 cm.

*Diameter.*—About 4 mm to 5 mm.

*Strength.*—Medium strong.

*Aspect.*—Upright to spreading.

*Texture.*—Smooth and glabrous.

*Color.*—Mature: RHS 145B. Immature: RHS 145A.

Branches:

*Branching habit.*—Basal branching with lateral branching.

*Number of branches per plant.*—About 10-15.

*Length* (*including flowers*).—About 13 cm to 16 cm.

*Diameter.*—About 4-5 mm.

*Strength.*—Medium strong.

*Apect.*—Upright to spreading.

*Texture.*—Smooth and glabrous.

*Color.*—Mature: RHS 145B. Immature: RHS 145A.

*Internode length.*—About 3 mm to 20 mm.

*Internode color.*—RHS 145A.

Foliage description:

*Arrangement.*—Alternate.

*Number of leaves per branch.*—About 8-12 per branch.

*Length.*—About 4 cm to 8 cm.

*Width.*—About 1.5 mm to 3.5 mm.

*Overall shape of leaf.*—Obovate to spatulate with 1 to 3 acuminate teeth on some of the leaves.

*Shape at apex.*—Obtuse to slightly retuse.

*Shape at base.*—Attenuate.

*Margin.*—Entire.

*Texture.*—Upper surface: Glabrous, with only a few scattered short, stiff hairs along on the edges of leaf. Lower surface: Glabrous.

*Color of developing foliage.*—Upper surface: RHS 137A. Lower surface: RHS 138A.

*Color of mature foliage.*—Upper surface: RHS 139A. Lower surface: RHS 137B.

*Venation pattern.*—Trinerved with veins along nerves.

*Venation color.*—Upper surface: RHS 145A. Lower surface: RHS 146C.

Inflorescence description:

*Arrangement and shape.*—Tubular disc floret and flat, lanceolate ray florets in composite flower heads, developed from terminal and axillary shoots. The peduncles lift the Inflorescences 2-4 cm above the foliage. Inflorescences face upright to 80° angle from vertical.

*Natural flowering season.*—*Osteospermum* is a bedding plant, with a flowering season from early spring to late autumn. Temperatures below 20° C. will increase flowering, temperatures above 20° C. will reduce flowering.

*Time to flower.*—65 to 85 days.

*Inflorescence longevity on the plant.*—Inflorescence will maintain good color and substance for about 5-10 days; however, the longevity of individual inflorescence is highly dependent on temperature and light conditions. Inflorescence persistent.

*Quantity of inflorescences heads.*—Freely flowering; about 40 buds and open inflorescences per plant.

*Fragrance.*—Sweet Honey.

*Bud* (*inflorescences head*).—Rate of opening (from showing color to fully open flower): 1 to 5 days. The rate of opening is highly dependent on temperature and light conditions. Length: About 10 mm. Diameter: About 8 mm. Shape: Acuminate. Texture: Pubescent with small hairs. Color: RHS 144A at base to 139B at apex.

*Peduncle.*—From both terminate and axillary shoots. Length: About 8 cm. Diameter: About 2 mm. Angle: About 0-20° from vertical. Strength: Medium strong. Texture: Pubescent with few small white hairs. Color: RHS 138A.

*Inflorescence head.*—Length: About 10 mm. Diameter: About 7 cm.

*Ray florets.*—Quantity per Inflorescence head: 20 - 24. Length: 32 mm. Widths: 8-9 mm. Overall shape: Spatulate. Shape at apex: Obtuse. Shape at base: Acute. Margin: Entire, small cleft at apex. Texture: Upper surface: smooth. Lower surface: smooth, matt slightly furrowed. Color upper side: Pure white. (as white as the space between the colour samples on The R.H.S. colour chart). Color underside: RHS 97C with darker stripes RHS 97A and stains of RHS 162C at the tip.

*Disc florets.*—Quantity per Inflorescence head: 75-85. Length: 6 mm. Diameter: 1 mm. Color Blue translucent (RHS 97A), white at base.

*Phyllary.*—20-25. Length: 9-11 mm. Width: 1-2 mm. Overall shape: Lanceolate. Apix: Narrow Acuminate. Base: Fused. Margin: Entire. Color: RHS 139B.

Reproductive organs:

*Androecium.*—Location: Disc florets only. Stamen number: 5 fused. Stamen length: About 2 mm. Anther shape: Linear, fused. Anther length: About 2 mm. Pollen amount: A lot. Pollen color: RHS N25C.

*Gynoecium.*—Location: Ray and disc florets. Quantity: 1. Pistil length: About 5 mm. Stigma shape: Brush-like, cleft 1.5 mm deep. Stigma length: About 2 mm. Stigma color: RHS 103A. Style length: About 2 mm. Style color: RHS 103C. Ovary color: RHS 144D.

Seed/fruit: Seed and fruit production has not been observed.

Disease/pest resistance: Resistance to pathogens and pests common to *Osteospermum* has not been observed.

Disease/pest susceptibility: Susceptibility to pathogens and pests common to *Osteospermum* has not been observed.

Temperature tolerance: Plants of the new *Osteospermum* have exhibited good tolerance rain, wind and drought; however, flowering may cease during hot periods (temperatures above 25° C.). Low temperature tolerance to 1° C.

What is claimed is:

1. A new and distinct cultivar of *Osteospermum* plant named 'DAOSFEMTEN', as illustrated and described herein.

* * * * *